United States Patent [19]
Tarumi et al.

[11] Patent Number: 5,936,111
[45] Date of Patent: Aug. 10, 1999

[54] FLUORINATED AMIDE COMPOUNDS WITH A PHENYL-SI-UNSATURATED GROUP

[75] Inventors: Yasuo Tarumi; Kenichi Fukuda; Masatoshi Arai, all of Usui-gun, Japan

[73] Assignee: Shin-Etsu Chemical Co., Ltd., Japan

[21] Appl. No.: 08/992,485

[22] Filed: Dec. 18, 1997

[30] Foreign Application Priority Data

Dec. 19, 1996 [JP] Japan .................................. 8-354533

[51] Int. Cl.$^6$ .................................................. C07F 07/10
[52] U.S. Cl. ........................... 556/419; 528/21; 528/32; 528/401
[58] Field of Search ................ 556/419; 528/21, 528/32, 401

[56] References Cited

U.S. PATENT DOCUMENTS 5,656,711  8/1997  Fukuda et al. ............................. 528/15
5,665,846  9/1997  Sato et al. ................................. 528/15

FOREIGN PATENT DOCUMENTS

| | | |
|---|---|---|
| 1-32227 | 6/1989 | Japan . |
| 1-188546 | 7/1989 | Japan . |
| 1-253044 | 10/1989 | Japan . |
| 2-311439 | 12/1990 | Japan . |
| 3-112938 | 5/1991 | Japan . |

*Primary Examiner*—Robert E. Sellers
*Attorney, Agent, or Firm*—Millen, White, Zelano, & Branigan, P.C.

[57] ABSTRACT

Fluorinated amide compounds of formula (1) wherein Rf is a perfluoroalkyl or perfluoropolyether group having 1 to 800 carbon atoms, R is hydrogen, methyl or phenyl, and letter a is 1, 2 or 3 are novel and useful as a modifier intermediate capable of improving various properties of silicone and liquid fluororubber.

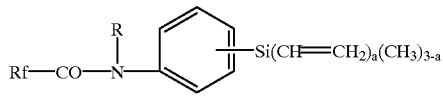

(1)

2 Claims, No Drawings

FLUORINATED AMIDE COMPOUNDS WITH A PHENYL-SI-UNSATURATED GROUP

BACKGROUND OF THE INVENTION

1. Field of the Invention

This invention relates to a novel fluorinated amide compound having a $\equiv$Si—CH=CH$_2$ group in a molecule and more particularly, to a fluorinated amide compound useful as a modifier intermediate capable of improving various properties of silicone and liquid fluororubber.

2. Prior Art

Compounds having a monovalent fluorinated organic group and an alkenyl group are known as a silicone modifying agent for improving various properties of silicone by introducing fluorine atoms therein. They are also useful as a main component of curable liquid fluororubber compositions utilizing hydrosilylation reaction. Several known compounds are shown below.

JP-A 253044/1989

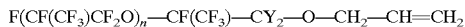

Y: fluorine or hydrogen
n: an integer of 1 to 4

JP-A 311439/1990

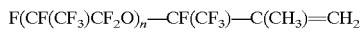

n: an integer of 1 to 4

JP-A 188546/1990

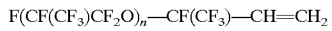

n: and integer of 1 to 4

JP-A 112938/1991

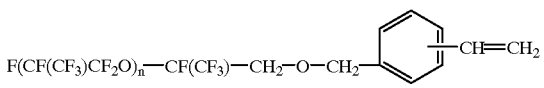

n: an integer of 1 to 3

These compounds are not necessarily satisfactory in reactivity as a silicone modifier because of the lack of the $\equiv$Si—CH=CH$_2$ structure.

JP-B 32227/1989 discloses (CF$_3$CH$_2$O)$_3$Si—CH=CH$_2$ which has the $\equiv$Si—CH=CH$_2$ structure. It is unsuitable as a silicone modifier because the $\equiv$Si—O—C$\equiv$ bond in its molecule is highly hydrolyzable.

SUMMARY OF THE INVENTION

An object of the present invention is to provide a novel fluorinated amide compound having the $\equiv$Si—CH=CH$_2$ structure useful as a modifier intermediate capable of improving various properties of silicone and liquid fluororubber.

We have found that a fluorinated amide compound of formula (1) is obtained by reacting a perfluorocarboxylic acid halide of formula (4) with an aniline derivative of formula (5) in the presence of an acid acceptor according to the following reaction scheme.

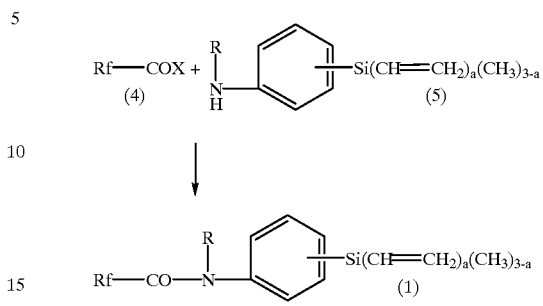

In the formulae, X is a halogen atom, Rf is a perfluoroalkyl or perfluoropolyether group having 1 to 800 carbon atoms, R is a hydrogen atom, methyl or phenyl group, and letter a is an integer of 1 to 3. The compound of formula (1) has a $\equiv$Si—CH=CH$_2$ group in its molecule, but not a hydrolyzable $\equiv$Si—O—C$\equiv$ bond. It is thus useful as a modifier intermediate capable of improving various properties of silicone and liquid fluororubber.

DETAILED DESCRIPTION OF THE INVENTION

The fluorine-containing amide compound of the invention is represented by the general formula (1):

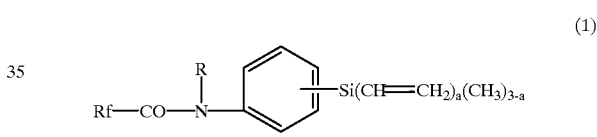

wherein Rf is a perfluoroalkyl or perfluoropolyether group having 1 to 800 carbon atoms, R is hydrogen, methyl or phenyl, and letter a is an integer of 1 to 3.

In formula (1), Rf is a perfluoroalkyl or perfluoropolyether group having 1 to 800 carbon atoms. The perfluoroalkyl groups are preferably those having 1 to 10 carbon atoms, for example, CF$_3$, C$_2$F$_5$, C$_3$F$_7$, C$_4$F$_9$, C$_5$F$_{11}$, C$_6$F$_{13}$, C$_7$F$_{15}$, CF$_8$F$_{17}$, C$_9$F$_{19}$, and C$_{10}$F$_{21}$.

The perfluoropolyether groups are preferably those having 3 to 800 carbon atoms, more preferably those of the general formula (2):

wherein Rf$^1$ is a monovalent perfluoroalkyl group having 1 to 10 carbon atoms, Rf$^2$ is a divalent perfluoroalkyl group having 1 to 6 carbon atoms, Rf$^3$ is —CF(CF$_3$)— or as defined for Rf$^2$, and letter q is an integer of 1 to 500.

In formula (2), Rf$^1$ is a monovalent perfluoroalkyl group having 1 to 10 carbon atoms, preferably 2 to 8 carbon atoms, examples of which are the same as exemplified for the perfluoroalkyl group represented by Rf. Rf$^2$ is a divalent perfluoroalkyl group having 1 to 6 carbon atoms, preferably 1 to 3 carbon atoms. Examples of the recurring unit represented by —(Rf$^2$—O)— include —CF$_2$O—, —CF$_2$CF$_2$O—, —CF(CF$_3$)O—, —CF$_2$CF$_2$CF$_2$O—, —CF(CF$_3$)CF$_2$O—, —CF$_2$CF$_2$CF$_2$CF$_2$O—, —$CF_2CF_2CF_2CF_2CF_2CF_2O$—, —$C(CF_3)_2O$—, and —$C(CF_3)_2CF_2O$—, with the —$CF_2O$—, —$CF_2CF_2O$—, —$CF_2CF_2CF_2O$—, and —$CF(CF_3)CF_2O$— being preferred. It is noted that the perfluoropolyether group of formula (2) may consist of recurring units —($Rf^2$—O)— of one type or different types. $Rf^3$ is —$CF(CF_3)$— or as defined for $Rf^2$. Letter q is an integer of 1 to 500, preferably 1 to 200.

In formula (1), R is a hydrogen atom, methyl or phenyl group, preferably methyl. Letter a is equal to 1, 2 or 3, preferably equal to 1.

Fluorinated amide compounds of formula (1) wherein Rf is a perfluoropolyether group derived from a polymer of hexafluoropropylene oxide are preferred since they are effective as a main component of of curable liquid fluororubber compositions utilizing hydrosilylation reaction. Specifically, the perfluoropolyether group represented by Rf is of the following formula (3):

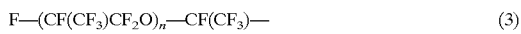

F—$(CF(CF_3)CF_2O)_n$—$CF(CF_3)$—     (3)

wherein letter n is an integer of 1 to 200.

The fluorinated amide compounds of formula (1) can be prepared by the following method, for example.

Specifically, they are prepared by reacting a perfluorocarboxylic acid halide of the following general formula (4) with an aniline derivative of the following general formula (5) in the presence of an acid acceptor.

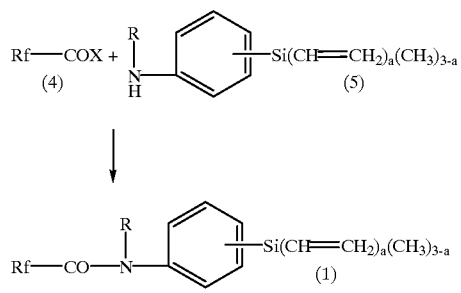

In the formulae, X is a halogen atom such as fluorine and chlorine, Rf, R, and a are as defined above. With respect to the mixing ratio of reactants, about 0.5 to 2 mol of the compund of formula (5) is used per mol of the compound of formula (4). Exemplary acid acceptors are triethylamine and pyridine. The amount of the acid acceptor used is about 1 to 1.5 mol per mol of the compound of formula (5). The reaction conditions, which are not critical, include a temperature of 20 to 100° C. and 1 to 8 hours, especially 20 to 70° C. and 2 to 4 hours.

At the end of reaction, the by-products of hydrogen halide and acid acceptor salt are removed by water washing and filtration. Alternatively, an SiN-containing compound such as $(CH_3)_3SiN(CH_3)_2$ and $(CH_3)_3SiNHSi(CH_3)_3$ is added to the reaction mixture to convert the salt into a liquid compound. Then the end product can be isolated by any suitable means of stripping, purification with the aid of activated carbon or distillation.

The fluorinated amide compounds thus obtained are useful as a modifier intermediate capable of improving various properties of silicone and liquid fluororubber.

There have been described fluorinated amide compounds having a ≡Si—CH=$CH_2$ group in their molecule which are useful as a modifier intermediate capable of improving various properties of silicone and liquid fluororubber. In particular, those compounds of formula (1) wherein Rf is a perfluoropolyether group of formula (3) are effective as a main component of of curable liquid fluororubber compositions utilizing hydrosilylation reaction.

EXAMPLE

Examples of the invention are given below by way of illustration and not by way of limitation.

Example 1

A 1-liter glass reactor equipped with a stirrer, condenser, thermometer, and dropping funnel was charged with 498 g of F—$(CF(CF_3)CF_2O)_2$—$CF(CF_3)$—COF. With stirring at 30° C. in a nitrogen stream, a mixture of 191 g of a compound of formula (6) shown below and 111 g of triethylamine was added dropwise over 2 hours.

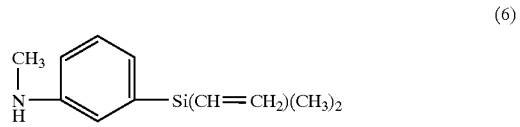

After the reaction mixture was stirred for 1 hour at 60° C., it was washed with water three times, dried over sodium sulfate, and filtered. Vacuum distillation yielded 535 g of a colorless clear liquid having a boiling point of 112° C. at 1 mmHg. On analysis, the product showed the following results, from which the product was determined to have the following structure.

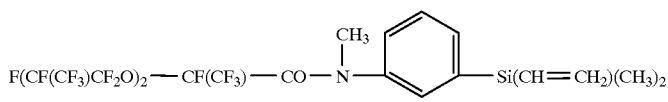

$^1$H-NMR

| | |
|---|---|
| δ 0.30 | (s, Si—$CH_3$, 6H) |
| δ 2.76 | (s, N—$CH_3$, 3H) |
| δ 5.4–6.2 | (m, —CH=$CH_2$, 3H) |
| δ 6.3–7.3 | (m, arom., 4H) |

-continued

| | Elemental analysis | | | | |
| --- | --- | --- | --- | --- | --- |
| | C | H | N | F | Si |
| Found (%) | 35.8 | 2.5 | 2.0 | 47.9 | 4.5 |
| Calcd. (%) | 35.9 | 2.4 | 2.1 | 48.2 | 4.2 |

Example 2

A 1-liter glass reactor equipped with a stirrer, condenser, thermometer, and dropping funnel was charged with 581 g of F—(CF(CF$_3$)CF$_2$O)$_n$—CF(CF$_3$)—COF wherein n had an average value of 34. With stirring at 60° C. in a nitrogen stream, a mixture of 21 g of a compound of formula (7) shown below and 12 g of triethylamine was added dropwise over 10 minutes. The reaction mixture was stirred for 1 hour at 60° C.

(7)

Next, 10 g of (CH$_3$)$_3$SiNHSi(CH$_3$)$_3$ was added dropwise over 10 minutes to the reaction solution, which was stirred for 1 hour at 60° C. The reaction solution was stripped for 3 hours at 150° C. and 1 mmHg and treated with activated carbon. By filtration, 544 g of a pale yellow clear oil was collected. The product was measured for physical properties, finding a viscosity of 1,500 centistokes at 25° C., a specific gravity of 1.82 at 25° C., an index of refraction of 1.322 at 25° C. A vinyl value of 0.017 mol/100 g was measured. From these analysis results, the product was determined to have the following structure.

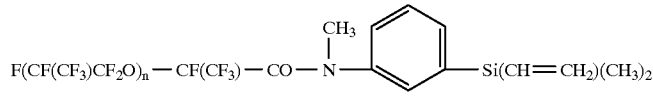

The average value of n is 33.4.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A fluorinated amide compound of the following general formula (1):

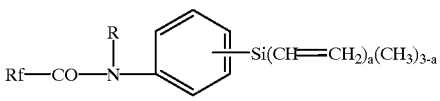

(1)

wherein Rf is a perfluoroalkyl or perfluoropolyether group having 1 to 800 carbon atoms, R is a hydrogen atom, methyl or phenyl group, and letter a is an integer of 1 to 3.

2. The fluorinated amide compound of claim 1 wherein Rf is a perfluoropolyether group of the following formula (3):

$$F-(CF(CF_3)CF_2O)_n-CF(CF_3)- \qquad (3)$$

wherein letter n is an integer of 1 to 200.

* * * * *